United States Patent [19]

Goode

[11] Patent Number: 4,556,122
[45] Date of Patent: Dec. 3, 1985

[54] EAR ACOUSTICAL HEARING AID

[75] Inventor: Richard L. Goode, Los Altos, Calif.

[73] Assignee: Innovative Hearing Corporation, San Francisco, Calif.

[21] Appl. No.: 557,701

[22] Filed: Dec. 2, 1983

Related U.S. Application Data

[63] Continuation-in-part of Ser. No. 297,723, Aug. 31, 1981, abandoned.

[51] Int. Cl.⁴ .............................................. G10K 11/26
[52] U.S. Cl. ..................................... 181/136; 181/129
[58] Field of Search ................ 181/129, 130, 133–136; 128/152

[56] References Cited

U.S. PATENT DOCUMENTS

| | | | |
|---|---|---|---|
| 345,025 | 7/1886 | Blodgett | 181/136 |
| 1,556,774 | 10/1925 | Fensky | 181/130 |
| 1,556,775 | 10/1925 | Fensky | 181/130 |
| 1,824,427 | 9/1931 | Fensky | 181/130 |
| 4,311,206 | 1/1982 | Johnson | 181/135 |

Primary Examiner—Benjamin R. Fuller
Attorney, Agent, or Firm—Flehr, Hohbach, Test, Albritton & Herbert

[57] ABSTRACT

An acoustical small hearing aid designed to be worn in the concha of the auricle and made of thin-walled plastic, metal, or rubber. This invention modifies the normal conchal resonance and combines it with the ear canal resonance to shift the normal sound pressure gain of 15 to 20 dB at the tympanic membrane downward from 2600–3000 Hz to 1500–2000 Hz dB, or lower, thus providing significant sound amplification for persons with mild high-frequency hearing loss. The invention accomplishes these goals by providing a thin, hollow shell that fits snugly into the auricle and concha of the external ear so as to enclose a volume of air within the concha. An opening in the shell lets sound waves into this air volume. The ratio of the air volume and the area of the opening control the peak frequency of amplification desired, the amplitude, and bandwidth of amplification, and must be kept between ½ and 1/15.

17 Claims, 7 Drawing Figures

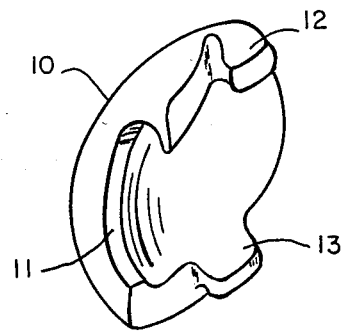
FIG.—1
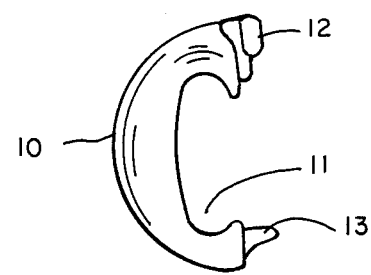
FIG.—2
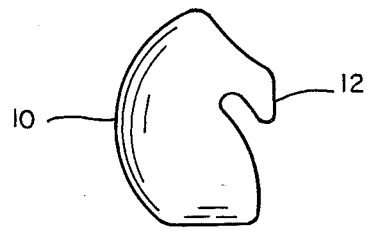
FIG.—3
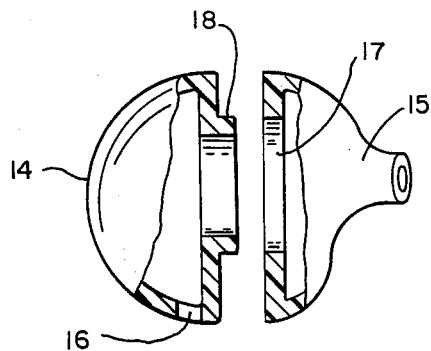
FIG.—4
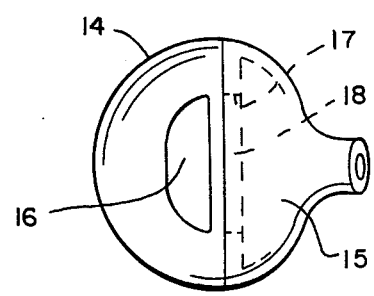
FIG.—5

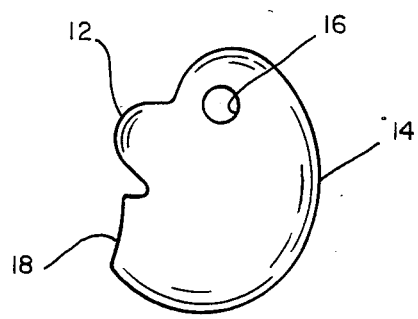
FIG.—6
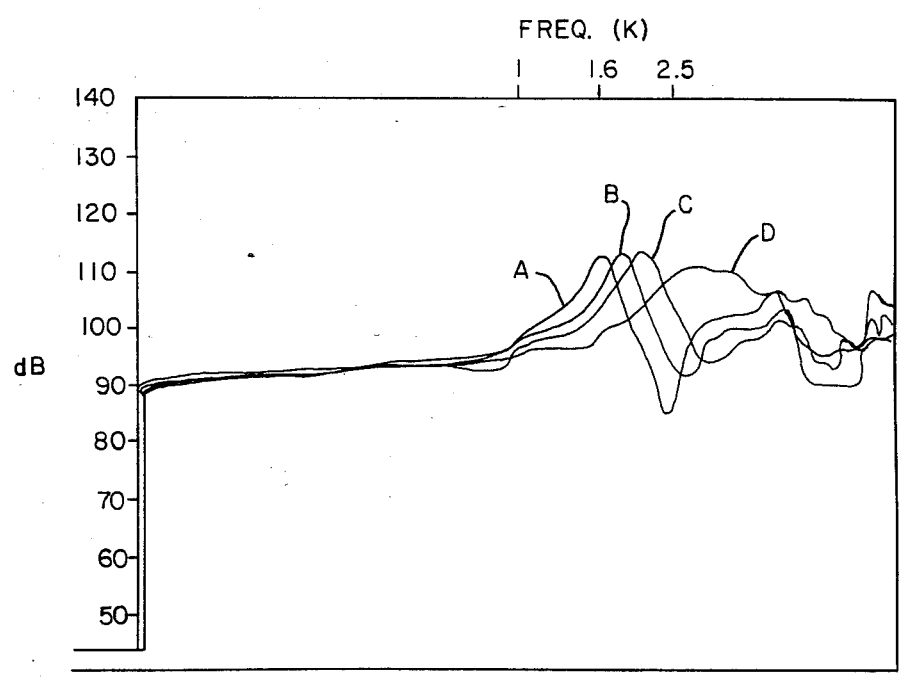
FIG.—7

EAR ACOUSTICAL HEARING AID

This application is a continuation-in-part of U.S. Application Ser. No. 297,723 filed Aug. 31, 1981 by Richard Goode abandoned.

This invention refers generally to a device for modifying the normal concha resonance and combining it with the ear canal resonance, shifting the sound pressure gain of 15 to 20 dB at the tympanic membrane downward from 2600–3000 Hz to 1500–2000 Hz or lower, thus providing a significant sound amplification for persons with mild hearing loss.

The present invention is capable of shifting the gain of the normal external ear to a lower frequency which is more useful for the understanding of speech. Such capability becomes important when hearing deficiencies become worse than 25 dB in important mid-frequency speech sounds. At this loss level a person is affected by the hearing loss. The major effect of this loss is difficulty in understanding speech, particularly when background noise is present. This happens because many important consonant sounds of speech lie within the 1500 to 3000 Hz frequency range. When the hearing loss becomes noticeable to a person, the only known effective treatment is to have an electronic hearing aid ordered for him. However, such hearing aid has a number of disadvantages including high cost, constant battery replacement, and other repair costs. Furthermore, when the hearing loss is mild (worse than 25 dB hearing level but better than 40 dB the person does not need sound amplification except in certain situations, such as meetings, church, and conversations whreer there is a some background noise. Thus an improved in-the-ear, non-electronic acoustical hearing aid providing significant hearing improvement for persons with mild hearing loss has been needed for many years.

The prior art included speaking tubes of varying lengths; horns held by hand to the patient's ear; and enlarged auricles (Pinnae) which were attached to the persons head. All these devices provide some sound amplification, but they are large, cumbersome, attention attracting and have been generally rejected by the public. There have been a number of small vibrating, sound concentrating devices designed to fit in the concha portion of the auricle or in the outer portion of the external ear-canal. Devices of this type have been cosmetically acceptable, but have inadequate amplification over an acceptable frequency range. In fact some of the devices shown in the prior art actually prevent sound from entering the ear, and are, for this reason, ineffective or valueless.

The reasons for the failure of all these small, non-electronic all in-the-ear acoustical devices to provide adequate improvement for the hearing impaired are clear only from detailed study. Three methods by which such devices are intended to work are:

1. Prevent collapse of the ear canal opening. Some patients have very narrow ear canal openings with soft cartilage. As a result of surgery, trauma or aging the opening may collapse and the hearing will be impaired. A small tube like device placed in the opening would keep the canal open. Several prior art devices appeared to function in this manner, but such work has no relationship to the present invention.

2. Act as attenuators of loud sound and noise. Many patients with sensorineural hearing loss due to cochlear hair cell damage have the phenomenon of "recruitment". With recruitment one may be barely able to hear a sound of moderate intensity, but a sound of slightly greater intensity is too loud. An acoustical device that produces an appropriate amount of attenuation in the recruiting frequencies would "improve" hearing by reducing the discomfort of louder sounds much as automatic gain control does on modern day electronic hearing aids.

3. Amplify sound by acting as a Helmholtz resonator. None of the devices in the prior art as exemplified by Fensky U.S. Pat. No. 1,556,774 directed to small, in-the-ear acoustical devices designed to be used alone (i.e. not in combination with an electronic hearing aid such as Johnson U.S. Pat. No. 4,311,206) effectively functioned as resonators of the Helmholtz type. They did not act as amplifiers but as attenuators. For example the device shown in the Johnson patent, when disconnected from the hearing aid it is designed to be used with, will because of the size of its opening, act as a low pass filter. This is because the Helmholtz formulas do not work except within certain critical boundaries defined herein. Some prior devices comprised in-the-ear acoustical hearing devices that contained vibrating tuning forks, reeds or diaphragms that resonate at a given frequency or frequencies so as to provide amplification at these frequencies. These device are entirely different from the present invention since they use a vibrating member. The status of in the ear non-electronic devices was well defined by Davis and Silverman in the 1970 edition of their book Hearing and Deafness (p. 283) when they said "restoration of hearing with a simple, inexpensive but miraculous gadget that fits comfortably within the ear canal is the dream of everyone who is hard of hearing. Even the most rational of us dream and wish."

The minimal amount of amplification required to be useful to a hearing impaired person comprises a gain of 5–10 dB in the 1–3 KHz range, a 10–15 dB improvement is helpful to almost all hearing impaired patients.

It is therefore a primary object of the present invention to provide a 5–15 dB increase in amplification of sounds in the 1000–3000 Hz range.

It is another object of the present invention to provide a non-electronic hearing aid that can be worn in the concha of the auricle to provide significant sound amplification of speech to correct mild hearing loss in the 1000–3000 Hz range.

It is a further object of the invention to provide a hearing device which is comfortable to wear, easy to insert and keep in place, and fast to remove and clean.

It is another object of the invention to provide a device which is non-electronic, and requires no batteries, springs, diaphragms, or moving parts.

In accordance with a preferred embodiment of the invention, this device comprises an acoustical resonator which modifies the normal resonance of the concha of the ear, shifts the resonant frequency downward from a normal conchal resonance of 4500 Hz to a frequency of about 2100 Hz. Such frequency is then combined with the ear-canal frequency; the invention operates to lower the normal conchal resonance by shifting the resonance peak at the tympanic membrane down to a point within the 1000–2500 Hz range with a bandwidth of several hundred Hz thus providing a 5–15 dB increase in sound pressure in this frequency range.

The subject invention comprises a small, all in-the-ear, hard walled device having a ratio of volume (in cc) to outside opening area ($mm^2$) of $\frac{1}{2}$ to 1/15. Changing the hole size or volume within the dimensions described shifts the peak frequency of amplification within the frequency range 1000-2500 Hz allowing it to be tuned. That is it has been found that by increasing the inlet hole size, the peak amplification frequency is raised.

The upper limit on volume is external appearance. Above a volume of 10 cc. appearance becomes a negative. The device can be made as one part or in two or more parts.

BRIEF DESCRIPTION OF THE DRAWING

FIG. 1 shows a curved chamber including also a chamber opening, the hooked chamber extensions keep the chamber snugly in place in the concha.

FIG. 2. shows the invention as it would appear to a person facing the user.

FIG. 3 shows a top view of the invention.

FIG. 4 shows an open shell ear-mold and dome of another embodiment of the invention.

FIG. 5 shows the ear-mold and dome matched together.

FIG. 6 shows an alternative embodiment of the invention.

FIG. 7 shows the channel amplification effects of the subject invention.

DETAILED DESCRIPTION OF THE PREFERRED EMBODIMENTS

Referring to FIG. 1, there is shown a thin chamber 10 which could assume a number of shapes. It is made of plastic, rubber, or metal, although the device will perform better when made of hard materials which should be sound reflective instead of sound absorbent. Preferred materials include acrylic plastic butyrate and acrylic plastic (Methyl-Methalcrylate); typically the acrylic shell is covered with vinly for ear comfort. The chamber fits snugly into the auricle and concha of the external ear so as to enclose a volume of air with the concha. Such volume may be between 6 and 10 cubic centimeters. As above mentioned the chamber could have a number of shapes, but esthetic and operational factors dictate that a circular chamber would be best suited for bouncing sound waves evenly. The chamber has an opening 11 for admitting sound into the chamber; Its best position is above and transverse to the longitudinal axis of the ear-canal, but it could be located in other positions. The size and shape of the inlet opening 11 can also vary; however, the volume enclosed within the chamber and the area of the opening control the peak frequency of amplification, the amount of amplification, and amplification bandwidth. The critical control ratio which ultimately limits any design is that the ratio of the volume enclosed (in cubic centimeters) to the area of the opening 11 (in square millimeters) should remain between ½ and 1/15 for the chamber to resonate at a useful frequency. The wall thickness of the chamber should be at least one millimeter for maximum reflectivity with minimum size.

In use, the chamber 10 fits snugly over the concha of the external ear. Such fit is achieved by means of the two hooked chamber extensions 12 and 13 which are formed by an extension of the upper and lower portions of the chamber. Elements 12 and 13 keep the device safely in place for the comfort of the user, and minimize sound leakage from the chamber. The chamber could be very small, but should not occlude the ear-canal.

The invention operates as an acoustical resonator that modifies the resonant frequency of the normal concha by shifting the resonant frequency downward from a normal conchal resonant frequency of about 4500 Hz, in the normal ear. The ear canal resonance for the average human ear is 3600 Hz. However, the presence of the concha, which can be thought of as a flared outer end of th ear canal adds an end-correction to the resonant frequency formula and thus lowers the peak resonant frequency to 2600-3000 Hz in the average human ear. At the resonant frequency there is found a pressure increase of about 12-15 dB SPL occurring at the ear drum.

In persons with mild hearing loss, this concha and ear-canal resonance peak of 15 dB at 2600-3000 Hz is not useful to provide sufficient information to enable the listener to understand what he hears. For an acoustical aid to be effective in aiding understanding of human speech, the peak resonance must somehow be shifted to occur in the lower portion of the 1000-3000 Hz range where the more important speech frequencies lie. The invention lowers the normal conchal resonance to be useful for persons with mild hearing loss by shifting the resonance peak at the tympanic membrane down to about 1700 Hz with a bandwidth of several hundred Hz and provides an increase in sound pressure of 5 to 17 dB at this frequency range.

The Helmholtz resonator formula is:

$$F_o = \frac{c}{2\pi} \sqrt{\frac{s}{l'V}}$$

where $f_o$=resonant frequency; c=speed of sound; s=area of opening; $2\pi$=6.28; $l'$=length of opening; V=volume.

In view of the small wall thickness of the opening in the device of about 1 mm., the ratio S/V is a very important parameter. Thus, when the opening area is enlarged, the volume remaining constant, the resonance frequency shifts upward. When the volume is enlarged, the opening area remaining constant, the resonance frequency shifts downward. The volume also determines the resonant peak or the "q" of the system. Thus, the larger the volume, the higher the resonance peak or "q", limited only by space availability in the auricle. On the other end, volumes smaller than 3 cc produce inadequate pressure gain. For example, the effect on the average ear of a chamber having a 7.9 cc volume and opening area of 119 square millimeters, the following pressure gains are obtained; at 1000 Hz, 5 dB; 1500 Hz, 10 dB; 1800 Hz, 15 dB; 2000 Hz, 10 dB; 2300 Hz, 1 dB. Thus by varying the volume of the chamber and the area of the opening maintaining the ratio between ½ and 1/15, the resonance frequency can be adjusted to meet specific hearing amplification needs of a person suffering from mild hearing loss. This effect is graphically demonstrated in FIG. 7 for various ratios of inlet hole size and internal volume, (A,B,C) as compared to normal open ear response (D).

It should be mentioned that above 10 cc's the volume of the chamber becomes too large to be desirable from an esthetic viewpoint. Volumes of 4 to 8 cc's with oval openings of about 3 to 8 mm diameter are optimal dimensions, particularly when the opening faces the direction of the incoming sound. As people with this type of hearing loss are affected in both ears, the device for each ear can be tuned at a slightly different frequency, and thus extend the bandwidth of the peak sound pressure amplification binaurally.

The above is a preferred embodiment of the invention. Other variations include a device made of two parts as shown in FIGS. 4 and 5: one a custom made ear-mold open shell 15 resulting from an impression of the concha and auricle and the other a dome 14 having a flange 18 which fits into an opening 17 of the ear-mold 15. The dome 14 has an opening 16 which admits the sound. The ratio of the area of opening 16 and the volume enclosed by parts 14 and 15 play the same dominant role as that described for the preferred embodiment of the invention and must be kept within the same limits of ½ to 1/15. FIG. 6 shows another embodiment of the same invention in which the dome 14 is molded to fit within the auricle of the ear. The shell portion fits within the concha has an opening 16 into the inner ear. The opening 16 is substantially perpendicular the transverse axis of the wearer's head.

Other embodiments of the invention may include a behind-the-ear configuration which disguises the volume. Then a freely vibrating surface may be placed at the sound admitting opening to help collect and direct the sound into the chamber. Other embodiments of this invention may occur to one of skill in the art who review this disclosure. Therefore the scope of the invention is to be limited only by the following claims.

What is claimed:

1. An acoustical hearing aid adapted for use in a human ear, comprising:
    a chamber having an opening on its surface to admit sound and an opening to pass sound to the inner ear, the chamber adapted to fit into the concha of the human ear and comprising a sound resonator having a bandwidth of several hundred hertz serving to shift a normal resonant frequency of the concha downward; and
    chamber extensions adapted to hook over the upper and lower aspects of the concha of the ear thus attaching said chamber to the auricle of the ear.

2. An acoustical hearing aid as recited in claim 1 in which the chamber opening is at a right angle to the longitudinal axis of the ear canal and facing the front plane of the face of the user.

3. An acoustical hearing aid as recited in claim 2 in which the chamber is made of sound reflective materials.

4. An acoustical hearing aid as recited in claim 3 in which the sound reflective material is acrylic plastic.

5. An acoustical hearing aid as recited in claim 4 in which the chamber is formed by curved surfaces and the ratio of the volume (in cubic centimeters) inside the chamber to the area (in square millimeters) of the chamber opening is in the range of ½ to 1/15.

6. An acoustical hearing aid adapted for use in a human ear, comprising:
    means for defining a hard walled acoustically resonant chamber adapted to fit in the concha of the ear, the end of the chamber having an opening facing the ear canal,
    the resonant chamber including a dome portion having an opening facing outward from the hearing aid to admit sound, the dome enclosing the volume adapted to operate as an acoustical resonator having a bandwidth of several hundred hertz serving to shift a normal resonant frequency of the concha downward.

7. An acoustical hearing aid as recited in claim 6 in which acoustic resonator dome portion comprises sound reflective material.

8. An acoustical hearing aid as recited in claim 7 in which the sound reflective material is acrylic plastic.

9. An acoustical hearing aid as recited in claim 8 in which the ratio of the volume (in cubic centimeters) enclosed by the resonant chamber to the area (in square millimeters) of the opening of the chamber is in the range from ½ to 1/15.

10. A self contained acoustical hearing aid adapted for use in a human ear, comprising:
    a chamber formed by curved surfaces and having an opening in the surfaces, the chamber adapted to fit into the concha of the human ear and operating as a sound resonator, serving to shift a normal resonant frequency of the concha downward, the opening being located at right angles to the longitudinal axis of the ear canal and facing the front plane of the face of the user, the ratio of the chamber volume (in cubic centimeters) to the area of the opening (in square millimeters) being in the range of ½ to 1/15.

11. A self contained acoustical hearing aid adapted for use in a human ear as recited in claim 10 which is made out of sound reflective acrylic plastic Butyrate.

12. A self contained acoustical hearing aid adapted for use in a human ear as recited in claim 10 which is made out of sound reflective acrylic plastic Methyl-Methacrylate.

13. A self contained hard-walled acoustical hearing aid comprising:
    a shell ear-mold adapted to fit in the concha and auricle of the ear, the end of the mold having an opening facing the ear canal, and a dome portion having an opening facing outward from the hearing aid, the dome and the open shell ear-mold enclosing a chamber adapted to operate as an acoustical resonator, the ratio of the chamber volume (in cubic centimeters) to the area (in square millimeters) of the second opening on the order of a range from ½ to 1/15, said chamber serving to shift a normal frequency of the concha downward.

14. A self contained acoustical hearing aid adapted for use in a human ear as recited in claim 13 which is made out of sound reflective acrylic plastic Butyrate.

15. A self contained acoustical hearing aid adapted for use in a human ear as recited in claim 13 which is made out of sound reflective acrylic plastic Methyl-Methacrylate.

16. A hearing aid as claimed in claim 2, 6, 10 or 13 wherein the chamber opening is about 3–8 $mm^2$.

17. A hearing aid as claimed in claim 2, 6, 10 or 13 wherein the internal volume of the chamber is about 4–8 ccs.

* * * * *

REEXAMINATION CERTIFICATE (750th)
United States Patent [19]
Goode

[11] B1 4,556,122

[45] Certificate Issued Aug. 18, 1987

[54] EAR ACOUSTICAL HEARING AID

[75] Inventor: Richard L. Goode, Los Altos, Calif.

[73] Assignee: Innovative Hearing Corporation, San Francisco, Calif.

Reexamination Request:
No. 90/001,045, Jun. 30, 1986

Reexamination Certificate for:
Patent No.: 4,556,122
Issued: Dec. 3, 1985
Appl. No.: 557,701
Filed: Dec. 2, 1983

[51] Int. Cl.$^4$ ............................................. G10K 11/26
[52] U.S. Cl. .................................... 181/136; 181/129
[58] Field of Search ............... 181/129, 130, 133–136; 128/152

[56] References Cited

U.S. PATENT DOCUMENTS

| | | | |
|---|---|---|---|
| 345,025 | 7/1886 | Blodgett | 181/136 |
| 1,556,774 | 10/1925 | Fensky | 181/130 |
| 1,556,775 | 10/1925 | Fensky | 181/130 |
| 1,824,427 | 9/1931 | Fensky | 181/130 |
| 4,311,206 | 1/1982 | Johnson | 181/135 |

FOREIGN PATENT DOCUMENTS 43052 1/1966 Fed. Rep. of Germany ...... 181/136

OTHER PUBLICATIONS

"Ear Resonator: A New Answer for Mild Hearing Loss", Richard L. Goode et al, Oct. 1982.
"Historic Devices for Hearing", CID–Goldstein Collection, Central Institute for the Deaf, Koelkebeck et al, 1984, pp. 1–59.
"The Hearing Aid, Its Operation and Development", The National Hearing Aid Society, K. W. Berger, 1970, 1974, pp. 117–139 and 7–24.

Primary Examiner—Benjamin R. Fuller

[57] ABSTRACT

An acoustical small hearing aid designed to be worn in the concha of the auricle and made of thin-walled plastic, metal, or rubber. This invention modifies the normal conchal resonance and combines it with the ear canal resonance to shift the normal sound pressure gain of 15 to 20 dB at the tympanic membrane downward from 2600–3000 Hz to 1500–2000 Hz dB, or lower, thus providing significant sound amplification for persons with mild high-frequency hearing loss. The invention accomplishes these goals by providing a thin, hollow shell that fits snugly into the auricle and concha of the external ear so as to enclose a volume of air within the concha. An opening in the shell lets sound waves into this air volume. The ratio of the air volume and the area of the opening control the peak frequency of amplification desired, the amplitude, and bandwidth of amplification, and must be kept between ½ and 1/15.

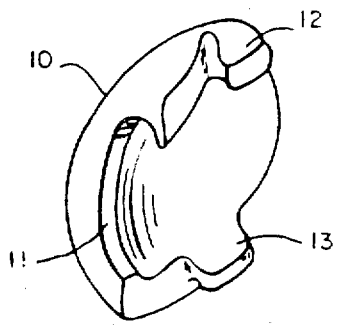

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 4–6:
[This application is a continuation-in-part of U.S. application Ser. No. 297,723 filed August 31, 1981 by Richard Goode abandoned.]

Column 3, lines 28–57:
Referring to FIG. 1, there is shown a thin chamber 10 which could assume a number of shapes. It is made of plastic, rubber, or metal, although the device will perform better when made of hard materials which should be sound reflective instead of sound absorbent. Preferred materials include acrylic plastic butyrate and acrylic plastic (Methyl-Methalcrylate); typically the acrylic shell is covered with vinyl for ear comfort. The chamber fits snugly into the auricle and concha (*shell-like portion of the auricle*) of the [external] ear so as to enclose a volume of air with the concha. Such volume may be between 6 and 10 cubic centimeters. As above mentioned, the chamber could have a number of shapes, but esthetic and operational factors dictate that circular chamber would be best suited for bouncing sound waves evenly. The chamber has an opening 11 for admitting sound into the chamber; Its best position is above and transverse to the longitudinal axis of the ear canal, but it could be located in other positions. The size and shape of the inlet opening 11 can also vary; however, the volume enclosed within the chamber and the area of the opening control the peak frequency of amplification, the amount of amplification and amplification bandwidth. The critical control ratio which ultimately limits any design is that the ratio of the volume enclosed (in cubic centimeters) to the area of the opening 11 (in square millimeters) should remain between ½ and 1/15 for the chamber to resonate at a useful frequency. The wall thickness of the chamber should be at least one millimeter for maximum reflectivity with minimum size.

Column 3, lines 58–65:
In use, the chamber 10 fits snugly [over] *within* the concha of the external ear. Such fit is achieved by means of the two hooked chamber extensions 12 and 13 which are formed by an extension of the upper and lower portions of the chamber. Elements 12 and 13 keep the device safely in place for comfort of the user, and minimize sound leakage from the chamber. The chamber could be very small, but should not occlude the ear-canal.

Column 5, line 1–17:
The above is a preferred embodiment of the invention. Other variations include a device made of two parts as shown in FIGS. 4 and 5: one a custom made ear-mold open shell 15 resulting from an impression of the concha and auricle and the other a dome 14 having a flange 18 which fits into an opening 17 of the ear-mold 15. The dome 14 has an opening 16 which admits the sound. The ratio of the area of opening 16 and the volume enclosed by parts 14 and 15 play the same dominant role as that described for the preferred embodiment of the invention and must be kept within the same limits of ½ to 1/15. FIG. 6 shows another embodiment of the invention in which the dome 14 is molded to fit within the auricle of the ear. The shell portion fits within the concha, and has an opening [16] *19* into the inner ear. The opening [16] *19* is substantially perpendicular the transverse axis of the wearer's head.

AS A RESULT OF REEXAMINATION, IT HAS BEEN DETERMINED THAT:

Claims 1, 3, 5, 6, 10 and 13 are determined to be patentable as amended.

Claims 2, 4, 7–9, 11, 12 and 14–17 dependent on an amended claim, are determined to be patentable.

New claims 18 and 19 are added and determined to be patentable.

1. An acoustical hearing aid adapted for use in a human ear, comprising:
a *curved hard-walled structure defining a chamber and* having an *outward facing* opening on [its] *a* surface *thereof* to admit sound [and an opening to pass sound] *into said chamber for passage* to the inner ear, [the chamber] *said hard-walled structure* adapted to fit into the *auricle and* concha of the human ear and [comprising] *to enclose a preselected volume of said chamber with the concha for providing* a sound resonator having a bandwidth of several hundred hertz serving to shift a normal resonant frequency of the concha downward; and [chamber] extensions *connected to the hard-wall of the chamber* adapted to hook over the upper and lower aspects of the concha of the ear thus attaching said chamber to the auricle of the ear.

3. An acoustical hearing aid as recited in claim 2 in which the *hard-wall of the* chamber is made of sound reflective materials.

5. An acoustical hearing aid as recited in claim 4 in which [the chamber is formed by curved surfaces and] the ratio of the volume (in cubic centimeters) inside the chamber to the area (in square millimeters) of the chamber opening is in the range of ½ 1/15.

6. An acoustical hearing aid adapted for use in a human ear, comprising:
[means for defining hard walled acoustically resonant chamber] *a curved hard-walled structure forming a shell having a dome portion and defining an acoustical resonator* adapted to fit in the concha of the ear, [the end of the chamber] *said shell* having an *end portion provided with an* opening facing the ear canal, the [resonant chamber including a] dome portion *including a resonant chamber of a preselected volume* having an opening facing outward from the [hearing aid] *ear* to admit sound, the dome enclosing the chamber volume to admit sound, the dome enclosing the *chamber* volume [adapted to operate] *operates* as an acoustical resonator having a bandwidth of several hundred hertz serving to shift a normal resonant frequency of the concha downward.

10. A self contained acoustical hearing aid adapted for use in a human ear, comprising:

a *preselected* chamber *volume* formed by *a* curved [surfaces] *hard surface* and having an opening in the [surfaces] *surface*, the *hard surface of the* chamber adapted to fit into the concha of the human ear and operating as a sound resonator, serving to shift a normal resonant frequency of the concha downward, the opening being located at right angles to the longitudinal axis of the ear canal and facing the front plane of the face of the user, the ratio of the chamber volume (in cubic centimeters) to the area of the opening (in square millimeters) being in the range of ½ to 1/15.

13. A self contained hard-walled acoustical hearing aid comprising:

a shell *structure defining an open shell* ear-mold adapted to fit in the concha and auricle of the ear, [the] *an* end *portion* of the mold having an opening facing the ear canal, and a *hollow hard-walled* dome portion having an opening facing outward from the [hearing aid, the dome inside and] *ear,* the open shell ear-mold [enclosing] *and the dome portion cooperating to enclose* a chamber *of a preselected volume* adapted to operate as an acoustical resonator, the ratio of the chamber volume (in cubic centimeters) to the area (in square millimeters) of the [second] opening *facing outwardly from the ear* on the order of a range from ½ to 1/15, said chamber serving to shift a normal frequency of the concha downward.

*18. An acoustical hearing aid as in claim 6 wherein the wall thickness of said hearing aid is at least one millimeter.*

*19. An acoustical hearing aid as in claim 6 wherein the chamber is located above and transverse to the longitudinal axis of the ear canal.*

* * * * *